United States Patent [19]
Johnson et al.

[11] Patent Number: 5,429,735
[45] Date of Patent: Jul. 4, 1995

[54] METHOD OF MAKING AND AMPEROMETRIC ELECTRODES

[75] Inventors: Larry D. Johnson, Mill Creek; Alison J. Murray, Elkhart; Matthew K. Musho, Granger, all of Ind.

[73] Assignee: Miles Inc., Elkhart, Ind.

[21] Appl. No.: 265,913

[22] Filed: Jun. 27, 1994

[51] Int. Cl.6 .............................................. G01N 27/26
[52] U.S. Cl. ................................... 204/403; 204/400; 204/402; 204/192.1; 204/298.01; 435/817
[58] Field of Search ........... 204/403, 412, 402, 298.01, 204/192.1, 157.43, 177, 418; 435/817

[56] References Cited

U.S. PATENT DOCUMENTS

| | | | |
|---|---|---|---|
| 4,676,854 | 6/1987 | Suzuki et al. | 156/151 |
| 4,844,784 | 7/1989 | Suzuki et al. | 204/180.9 |
| 5,002,652 | 3/1991 | Nelson et al. | 204/412 |
| 5,264,103 | 11/1993 | Yoshioka et al. | 204/403 |

*Primary Examiner*—Niebling: John
*Assistant Examiner*—Bruce F. Bell
*Attorney, Agent, or Firm*—Jerome L. Jeffers

[57] ABSTRACT

A method of making and an amperometric electrode are provided. An electrode carbon ink is applied to a polymer substrate to form a working electrode. The substrate carrying the working electrode is placed in a gas plasma cleaner, such as an oxygen or nitrogen plasma, to clean the working electrode. A high radio frequency signal excites the gas plasma for a short exposure time in a range between 10 seconds and 30 seconds. Then a reagent layer is deposited to the plasma treated working electrode.

15 Claims, 2 Drawing Sheets

METHOD OF MAKING AND AMPEROMETRIC ELECTRODES

BACKGROUND OF THE INVENTION

1. Field of the Invention

The present invention generally relates to biosensors, and, more particularly, to new and improved amperometric electrodes and a method of making the amperometric electrodes.

2. Description of the Prior Art

Amperometric electrodes, or biosensors, such as a glucose biosensor, are used for electrochemical measurements. In operation, a sample is applied to the amperometric electrodes, and a resulting current is measured for a test sample. The resulting current should have sufficient magnitude to facilitate measurement and have reproducibility to provide a meaningful test result.

Time consuming and undesirable processes, such as polishing and heat treatment, have been required for known amperometric electrodes to achieve the required current response. A need exists for amperometric electrodes providing reliable, reproducible and effective operation that are simple and economical to manufacture.

SUMMARY OF THE INVENTION

Important objects of the present invention are to provide a new and improved method of making and amperometric electrode; to provide amperometric electrodes that provide reliable, reproducible and effective operation and to provide amperometric electrodes for a blood glucose biosensor.

In brief, the objects and advantages of the present invention are achieved by a method of making and an amperometric electrode. An electrode carbon ink is applied to a polymer substrate to form a working electrode. The substrate carrying the working electrode is placed in a gas plasma cleaner, such as an oxygen or nitrogen plasma, to clean the working electrode. A high radio frequency signal excites the gas plasma for a short exposure time in a range between 10 seconds and 30 seconds. Then a reagent layer is deposited to the plasma-treated working electrode.

BRIEF DESCRIPTION OF THE DRAWING

The present invention, together with the above and other objects and advantages, can best be understood from the following detailed description of the embodiment of the invention illustrated in the drawing, wherein.

DETAILED DESCRIPTION OF THE PREFERRED EMBODIMENT

Figure 1:
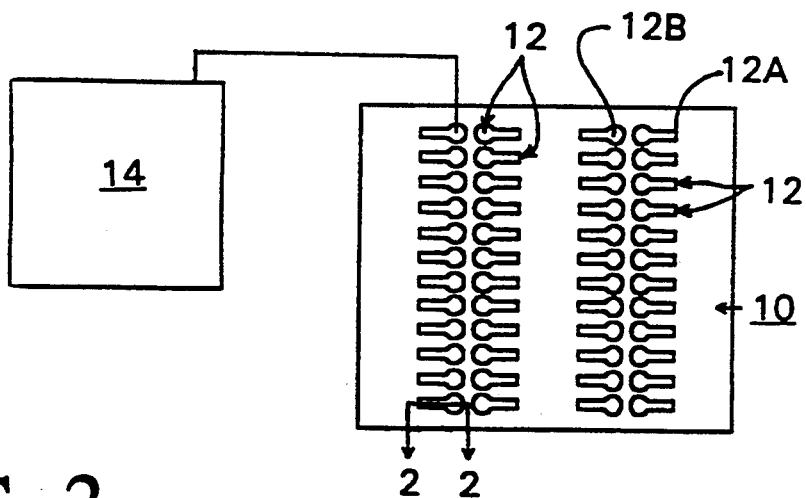
FIG. 1 is a schematic and plan view of a sensor card including a plurality of amperometric electrodes of the present invention.
Figure 2:
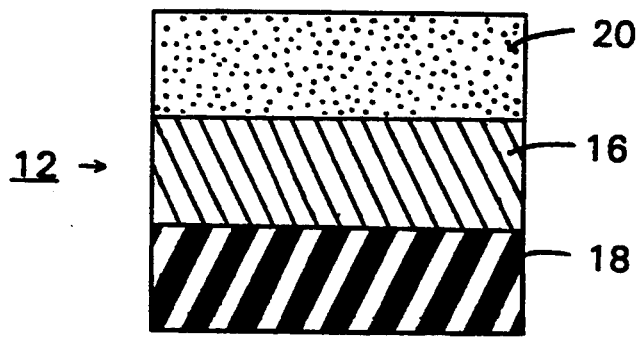
FIG. 2 is an enlarged sectional view of the amperometric electrode taken along line 2—2 of FIG. 1.

Referring now to FIGS. 1 and 2, there is shown a sensor card 10 including a plurality of amperometric electrodes 12 of the present invention. Amperometric electrodes 12 include an end portion 12A for receiving a test sample and an opposite end lead/contact pad portion 12B for connection with an instrument 14 capable of imposing a voltage potential and measuring the resulting current. The amperometric electrodes 12 include a working electrode 16 formed by an electrode carbon ink, for example, by screen printing onto a polymer substrate 18 and then thermally drying. A reagent layer 20 is deposited over the working electrode 16 after the working electrodes have been plasma treated in accordance with the present invention.

A thermoplastic material, such as a polycarbonate or polystyrene, having sufficient physical and electrical insulating properties can be used for the polymer substrate 18. The electrode carbon ink forming the working electrodes 16 can contain 18% graphite and 6% carbon black. For another example of the amperometric electrodes 12, the working electrodes 16 can be formed with an Acheson 423ss ink screen printed onto a polystyrene substrate 18.

Figure 3:
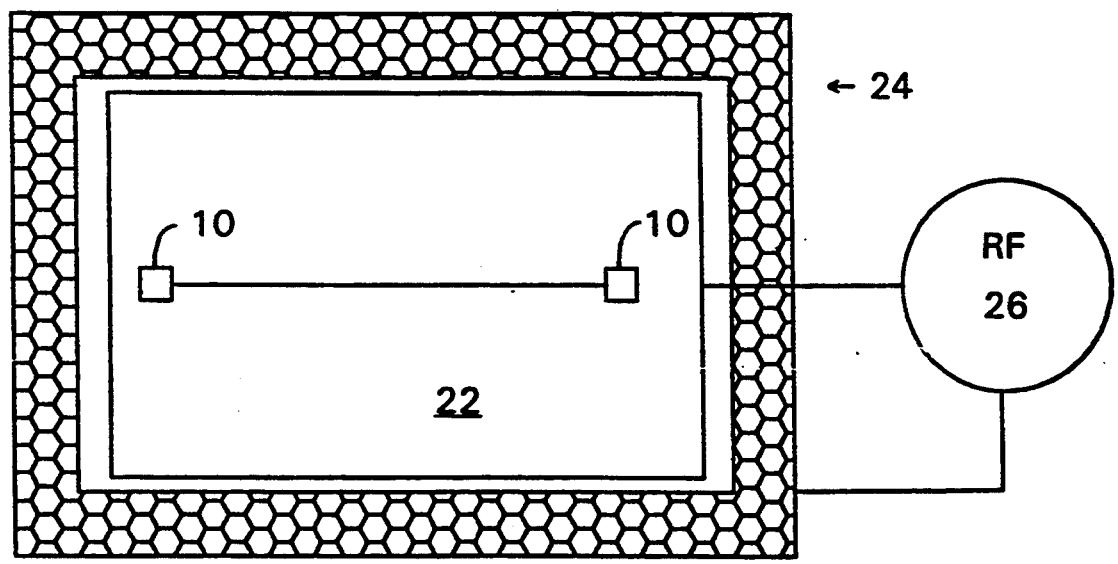
FIG. 3 is a schematic and block diagram representation of a plasma cleaner for use in the process of making the amperometric electrodes of FIG. 1.

Referring also to FIG. 3, sensor cards 10 with carbon working electrodes 16 are thermally dried and then placed into a chamber 22 of a plasma cleaner 24. A small barrel plasma etcher sold by March Instruments can be used for the plasma cleaner 24. The chamber 22 is first evacuated to 0.1–0.2 Torr and then backfilled with a gas, such as oxygen ($O_2$) or nitrogen ($N_2$), to an operating pressure of 0.3–0.5 Torr. Once the pressure stabilizes, the gas is excited by a radio frequency (RF) signal source 26 having a frequency of 13.56 Mhz and a power level typically of 20–25 watts. The cavity is tuned to maintain zero reflected power. After a selected time period, such as 30 seconds, of RF gas plasma treatment, the sensor cards 10 are removed from the chamber 22 and are ready for chemistry deposition or testing. Then the reagent layer 20 containing an enzyme, such as glucose oxidase for a blood glucose biosensor, and a mediator or electron transfer agent is deposited over the treated surface of the working electrode 16.

Photomicrographs of the carbon working electrodes 16 before and after the gas plasma treatment do not show any observable physical change. However, the current response of the untreated and treated carbon working electrodes 16 are significantly different. Erratic behavior with little or no current is replaced by high, reproducible currents for the gas plasma treated electrodes 16. Polymeric binders such as polyvinyl chloride that are deposited with the carbon during screen printing of the working electrodes 16 are believed to be the primary material removed during the gas plasma cleaning treatment.

Figure 4:
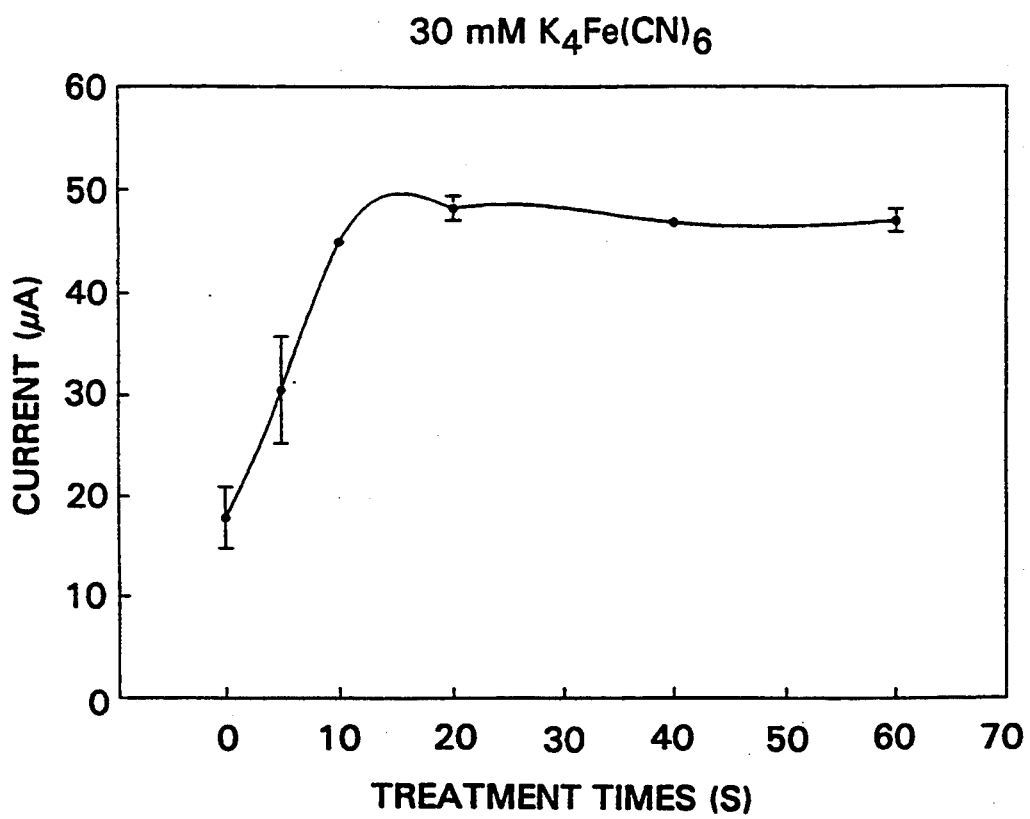
FIG. 4 is a graph illustrating the effect of plasma treatment time on the performance of the amperometric electrodes of FIG. 1.

FIG. 4 illustrates the effect of plasma treatment time on the performance of the amperometric electrodes 16. Treatment time is shown in seconds along the horizontal axis with a resulting current for the test solution in micro-amperes $\mu A$ shown along the vertical axis. For the results in FIG. 4, sensors were constructed by screen printing two carbon electrodes 16 using Acheson 423ss ink onto a polystyrene substrate 18. Two other printings were provided; one for the leads/contact pads 12B and another for an overcoat dielectric layer which protects the leads/contact pads 12B from the test solution. A selected plasma treatment time was provided, as illustrated in FIG. 4. A test solution of 6 μL aliquot of buffered, 30 mM potassium ferrocyanide $K_4Fe(CN)_6$ was applied to each sensor, and a time delay of 15 seconds was provided before a 0.4 volt potential was applied to the electrodes 16. The resulting current was measured 15 seconds after the 0.4 volt potential was initiated.

Figure 5:
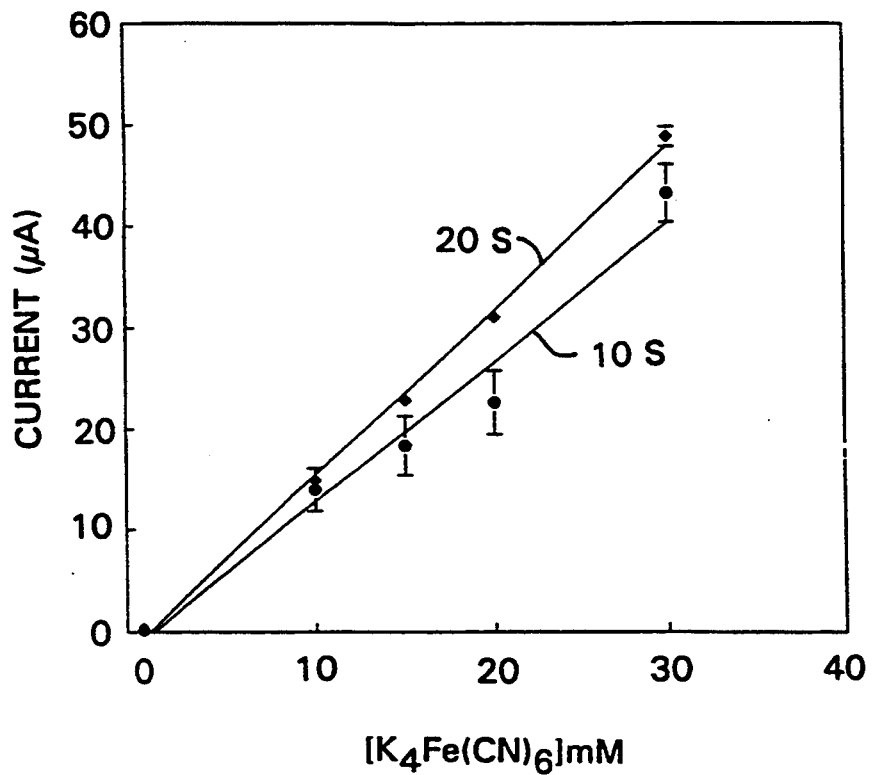
FIG. 5 is a graph illustrating the effect of a testing solution concentration on the performance of the amperometric electrodes of FIG. 1.

For FIG. 5 the same protocol as described with respect to FIG. 4 was used, except that the testing solution concentration was varied over the range of 0 to 30 mM potassium ferrocyanide. In FIG. 5 the testing solution concentration is shown along the horizontal axis with a resulting current for the test solution in microamperes μA shown along the vertical axis. Two plasma-cleaning times of 10 seconds and 20 seconds are illustrated by a line labelled 10S and a line labelled 20S, respectively.

The resulting current corresponds to the reduced mediator of the reagent layer 20. Typically the reagent layer is based on an aqueous polymer solution containing the required reagents for a particular biosensor.

EXAMPLE I

Procedure for Plasma Etching and Testing Electrode Cards

Electrodes are constructed using conductive and dielectric inks printed on a 3"×3" polycarbonate substrate. Conductive ink used for the active areas (electrodes—both working and reference) is Acheson 421ss which is screen printed on and then thermally cured. The areas of the electrodes are defined by an overcoat of dielectric (Acheson 452ss) which is screen printed on and then UV cured. Activating the printed electrodes requires treating cards in a plasma etcher. In our case we used either a small barrel-cavity instrument from March Instruments or a tray instrument from Branson/IPC. Cards are loaded on the shelves of a Branson/IPC plasma etcher. The plasma treater is evacuated to 0.1-0.2 torr, then backfilled with purified oxygen gas to a pressure of 0.8 torr. After a plasma is generated, the cards are treated for three minutes at 300 watts of power. Testing the activated electrodes requires that each sensor's leads be connected to a potentiostat for testing. This can be done in the card format or as singulated electrodes. The electrodes themselves are dipped into a solution containing 200 mM potassium Ferricyanide, 12.5 mM Potassium Ferrocyanide and 100 mM phosphate buffer pH 7. A positive 400 millivolts are applied across the working and reference electrodes, and the current is measured at the working electrode. With cards that have been plasma etched having a working electrode area of approximately 1 mm current will be 8-9 uamps after ten seconds with between sensor coefficients of variation (CVs) of less than 2%. If the electrodes were not plasma treated, the current would be 4-5 microamperes after ten seconds with CVs higher than 20%.

While the invention has been described with reference to details of the illustrated embodiment, these details are not intended to limit the scope of the invention as defined in the appended claims.

What is claimed is:

1. A method of making an amperometric electrode comprising the steps of:
   providing a substrate;
   applying an electrode carbon ink to said substrate to form a working electrode; said electrode carbon ink containing set amounts of graphite and carbon black;
   cleaning said working electrode utilizing a gas plasma; said gas plasma is a nitrogen gas plasma or an oxygen gas plasma; and
   depositing a reagent layer to said working electrode after said cleaning step.

2. A method of making an amperometric electrode as recited in claim 1 wherein said step of providing a substrate includes the step of providing a polymer substrate.

3. A method of making an amperometric electrode as recited in claim 1 wherein said step of applying an electrode carbon ink to said substrate includes the steps of screen printing said electrode carbon ink to said substrate to form said working electrode; and thermally drying said screen printed working electrode.

4. A method of making an amperometric electrode as recited in claim 1 wherein said step of applying said electrode carbon ink containing set amounts of graphite and carbon black includes applying an electrode carbon ink containing approximately 18% graphite and 6% carbon black.

5. A method of making an amperometric electrode as recited in claim 1 wherein said step of cleaning said working electrode utilizing a gas plasma includes the steps of:
   placing said substrate carrying said working electrode in a chamber;
   evacuating said chamber in a range between 0.1 to 0.2 Torr;
   backfilling said evacuated chamber with a gas to an operating pressure in a range between 0.3 to 0.5 Torr; and
   exciting said gas with a radio frequency (RF) signal.

6. A method of making an amperometric electrode as recited in claim 5 wherein said step of exciting said gas with a radio frequency (RF) signal includes the steps of:
   identifying said operating pressure stabilized at a set pressure; and
   applying said radio frequency (RF) signal having a set frequency of about 13.56 Mhz with a set power level of 20 to 25 watts.

7. A method of making an amperometric electrode as recited in claim 5 wherein said step of exciting said gas with a radio frequency (RF) signal includes the step of applying a radio frequency (RF) signal having a frequency of about 13.56 Mhz for a selected time period in a range between 10 seconds and 30 seconds.

8. A method of making an amperometric electrode as recited in claim 1 wherein said step of depositing a reagent layer to said working electrode after said cleaning step includes the step of depositing a layer containing an enzyme and an electron transfer agent over said cleaned working electrode.

9. A method of making an amperometric electrode as recited in claim 1 wherein the amperometric electrode is used for a glucose biosensor and wherein said step of depositing a reagent layer to said working electrode after said cleaning step includes the steps of depositing a layer containing a glucose oxidase.

10. A method of making an amperometric electrode as recited in claim 1 wherein said step of providing a substrate includes providing a substrate formed of an electrical insulative, thermoplastic material.

11. An amperometric electrode comprising:
    an electrical insulative substrate formed of thermoplastic material;

a working electrode carried by said substrate; said working electrode is formed by an electrode carbon ink containing graphite and carbon black; said working electrode is cleaned by a gas plasma; said gas plasma is a nitrogen gas plasma or an oxygen gas plasma; and a reagent layer deposited to said gas plasma treated working electrode.

12. An amperometric electrode as recited in claim 11 wherein said working electrode is formed by said electrode carbon ink containing approximately 18% graphite and 6% carbon black.

13. An amperometric electrode as recited in claim 11 wherein said working electrode is formed by screen printing said electrode carbon ink onto said electrical insulative substrate.

14. An amperometric electrode as recited in claim 11 wherein said working electrode is treated by said gas plasma by exciting said gas with a radio frequency (RF) signal having a frequency of about 13.56 Mhz.

15. An amperometric electrode as recited in claim 11 wherein said working electrode is treated by said gas plasma by exciting said gas with a radio frequency (RF) signal having a set frequency of about 13.56 Mhz with a predetermined power level of 20 to 25 watts.

* * * * *